United States Patent [19]

Klein

[11] Patent Number: 5,785,949
[45] Date of Patent: Jul. 28, 1998

[54] MEASUREMENT OF LIQUID PHASE GASTRIC EMPTYING

[75] Inventor: Peter D. Klein, Houston, Tex.

[73] Assignee: Meretek Diagnostics, Houston, Tex.

[21] Appl. No.: 711,405

[22] Filed: Sep. 5, 1996

[51] Int. Cl.$^6$ .............................. A61K 51/00; A61M 36/14
[52] U.S. Cl. .................. 424/1.81; 424/1.11; 424/1.17; 424/1.65; 424/439; 435/4; 435/29
[58] Field of Search ........................... 435/29, 804, 3, 435/4, 7.2, 257.1, 243; 424/1.11, 1.17, 1.37, 1.65, 1.81, 400, 439; 426/282, 283, 531, 549, 653

[56] References Cited

U.S. PATENT DOCUMENTS

| | | | |
|---|---|---|---|
| 5,140,993 | 8/1992 | Opekun, Jr. et al. | 128/730 |
| 5,233,997 | 8/1993 | Klein et al. | 128/718 |

OTHER PUBLICATIONS

Bjorman et al (1989), vol. 96, No. 5, Part 2, p. A46, "Comparison of the 13C Bicarbonate Breath Test with radiolabeled Meals in Gastric Emptying." (Gastroenterology).

Klein et al (1987), vol. 92, No. 5, Part 2, p. 1470, "The 13C-Bicarbonate Meal Breath Test: A New Noninvasive Measurement of Gastric Emptying of Liquid or Solid Meals". (Gastroenterology).

Maes et al. (1996), Gut, vol. 38, pp. 23–27, "Relation between gastric emptying rate and rate of intraluminal lipolysis".

Maes et al (1994), Journal of Nuclear Medicine, vol. 35, No. 5, pp. 824–831, "Combined Carbon–13 Glycine/Carbon–14–Octanoic Acid Breath Test to Monitor Gastric Emptying Rates of Liquids and Solids".

Maes et al (1995), Gut, vol. 36, pp. 183–188, "Relation between gastric emptying rate and energy intake in children compared with adults".

Article entitled "The |13C]Acetate Breath Test Accurately Reflects Gastric Emptying of Liquids in Both Liquid and Semisolid Test Meals", by Barbara Braden, Stefan Adams, Li–Ping Duan, Karl–Heinz Orth, Frank–Dieter Maul, Bernhard Lembcke, Gustav Hor and Wolfgang F. Caspary, Gastroenterology, vol. 108, No. 4, pub. Apr., 1995, pp. 1048–1055 (8 pages).

*Primary Examiner*—John Kight
*Assistant Examiner*—Dameron Jones
*Attorney, Agent, or Firm*—Bush, Riddle & Jackson

[57] ABSTRACT

A drink adapted to be consumed by a patient to enable measurement of gastric emptying of the liquid phase, is a fruit juice having mixed and suspended therein a quantity of Spirulina platensis alga grown in a $^{13}CO_2$ atmosphere. These single cell organisms pass from the stomach into the small intestine where they are digested, absorbed and oxidized to produce a detectible rise in the level of $^{13}CO_2$ in the patient's breath which is sampled and the measured valves plotted to enable determination of gastric emptying rate abnormalities.

7 Claims, 1 Drawing Sheet

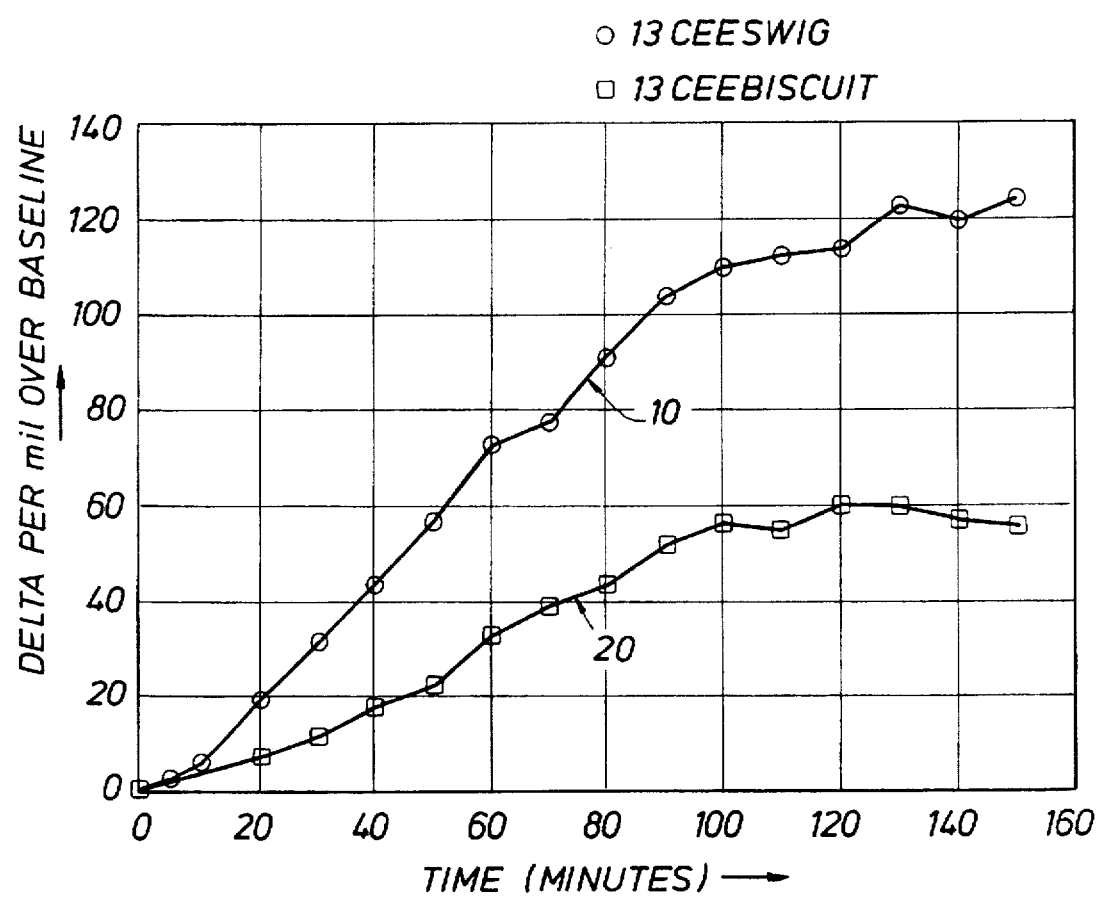

MEASUREMENT OF LIQUID PHASE GASTRIC EMPTYING

FIELD OF THE INVENTION

This invention relates generally to diagnosis of gastrointestinal disorders in humans, and particularly to measurement of the rate at which the liquid phase of food being digested in the stomach is emptied into the small intestine and whether such rate is abnormal.

BACKGROUND OF THE INVENTION

Digestion of all foods in humans begins in the stomach where both liquids and solids are mixed with gastric juice that is secreted by the walls of the stomach. The gastric juice is predominately hydrochloric acid, but also includes enzymes that break down food constituents so that they can be absorbed in the blood and used by the body. The contents of the stomach are emptied into the small intestine through the pyloric sphincter which opens and closes to release pulses of the mixture of solids and liquids. The rate of such emptying is regulated by this sphincter, and takes place more rapidly in the case of liquids than solids, however both are determined by the calorie content of the meal. The higher the calorie content, the slower the discharge rate. In addition, the solid phase of the food must undergo comminution, or reduction in particle size, caused by contractions of the stomach until a particle size of about 1 mm in diameter is reached.

A disorder can result in either accelerated or delayed emptying. Accelerated emptying causes the food to be "dumped" into the small intestine prematurely. Delayed emptying often is encountered in diabetic patents and may be associated with abdominal pain and cramping. Although medications or drugs have been developed to increase the rate of gastric emptying, their efficacy still is under investigation.

Diagnosis and measurement of gastric emptying has been possible only at highly specialized nuclear medicine facilities. The testing requires use of one radioactive tracer for the liquid phase and a second radioactive tracer for the solid phase. The movement of the radioactive tracers is monitored by positioning the recumbent patient between two large gamma ray responsive scintillation detectors or counters which measure the position and quantity of each isotope from the patient's anterior and posterior. This procedure requires 3-4 hours or more to perform.

The introduction of a radioactive tracer into the liquid phase of food poses no particular problem if the tracer is totally soluble, because the tracer then is miscible with the gastric juice and is emptied from the stomach coincident with the movement of the liquid phase. The solid phase marker is made somewhat difficult because it must be attached to the protein in a manner such that it is not leached out by the gastric juice, but sticks to individual particles and is lost from them only when they undergo enzymic digestion in the small intestine. Methods of attachment have included adding the tracer to a raw egg which then is scrambled and fed as a sandwich, and "sizzling" the isotope with a chicken liver puree and mixing the semi-solid food mass with a snack can of beef stew which then is consumed by the patient.

Recently, other liquid and solid phase tracers have been proposed. These tracers are $^{13}C$ labeled molecules which, when absorbed from the intestine, are rapidly oxidized to carbon dioxide ($CO_2$). The oxidation can be detected from an increase in the concentration of $^{13}CO_2$ in the breath that is exhaled by the patient. These substrates or tracers have the advantages that they are nonradioactive and thus do not expose the patient to radiation, and that breath samples can be collected without the use of invasive procedures. For example, sodium 1-$^{13}C$-acetate has been used as a liquid-phase marker, and the appearance of labeled $CO_2$ after substrate administration in a liquid meal has been correlated with the emptying of a radioactive liquid phase marker that is administered simultaneously.

However a potential problem exists with the use of such a small molecule. An increase in the permeability of the stomach wall, caused by disease or the use of certain drugs, can enable the molecule to pass between the cells of the lining of the stomach and thereby enter the blood stream directly. When that occurs, labeled $CO_2$ appears in the breath in an accelerated manner, and provides an appearance of earlier emptying than actually exists.

A unique solid phase emptying marker has been disclosed and claimed in my U.S. Pat. application Ser. No. 08/619,140 filed Mar. 25, 1996. This marker is an edible photosynthetic alga that is incorporated into a bread such as a biscuit that is consumed by the patient along with other food stuffs including a small portion of a fruit juice to bring the total caloric value of the meal to about 340. The present invention relates to a unique liquid phase marker that utilizes a cell suspension that is unable to penetrate the gastric mucosa, but instead passes with the liquid phase into the small intestine to enable gastric emptying to be reliably measured.

The general object of the present invention is to provide a new and improved measurement technique for determining liquid phase gastric emptying in a more reliable, safe and accurate manner.

Another object of the present invention is to provide a new and improved technique for measuring liquid phase gastric emptying through use of intrinsically marked single cell organisms suspended in a way such that they are unable to penetrate the gastric mucosa, and thus pass into the small intestine with the liquid phase to permit reliable measurement of gastric emptying of that phase.

SUMMARY OF THE INVENTION

These and other objects are attained in accordance with the concepts of the present invention through the provision of a method and means for measuring gastric emptying of the liquid phase which employs intrinsically labeled single cell organisms as a marker for such liquid phase. The organism is *Spirulina platensis*, an edible photosynthetic alga which has been grown in an atmosphere of 99% $^{13}CO_2$ so that all its carbons are $^{13}C$. A 500 mg portion of this marker is added to a 120 ml. bottle of white grape juice and mixed therein by shaking to form a product which then is consumed by the patient. At the same time, a biscuit prepared as disclosed herein is spread with cream cheese and is consumed by the patient to provide the solid portion of the test/meal, such test meal having a total, predetermined caloric composition that is the same or substantially the same as that used to test solid phrase gastric emptying time in accordance with the above-referenced application for patent. Breath samples are collected at 10 minute intervals over the next 120 minutes, and are analyzed for gastric emptying time of the liquid phase of the food by comparing $^{13}CO_2$ content of samples with base line data previously obtained from the patient after a period of fasting.

BRIEF DESCRIPTION OF THE DRAWINGS

The present invention has the above as well as other objects, features and advantages which will become more clearly apparent in connection with the following detailed description of a preferred embodiment, taken in conjunction with the appended drawing in which:

The drawing FIGURE is a graph showing change in concentration of $^{13}C$ in breath samples with time, the upper curve 10 representing the liquid phase measurement in accordance with this invention, and compared to exemplary solid phase data shown as the lower curve 20.

DETAILED DESCRIPTION OF A PREFERRED EMBODIMENT

In accordance with the present invention, the unique ingredient that is used to prepare a liquid phase emptying marker is an edible photosynthetic alga, *Spirulina platensis*, which has been grown in an atmosphere of 99% $^{13}CO_2$. On account of this growing process, all carbons contained in such alga are $^{13}C$. Each alga is a single-celled organism that is only several microns in diameter. The quantity of alge required to produce a detectable test signal has been found to be quite small. A certain quantity of such alge is suspended in a liquid as explained further below, and is consumed by the patient along with an unlabeled form of the biscuit or roll as a solid phase marker.

The edible biscuit is made from a dough recipe that has a calorie content of about 150. The biscuit contains carbohydrates, protein, and fat and preferably is packaged with an individual portion of cream cheese which contains 100 calories. When consumed with the grape juice, the total calorie value is about 340. A recipe by which four (4) of these biscuits can be made has the following ingredients:

- 100 g. wheat flour
- 50 g. rye flour
- 90 ml. cold coffee
- 10 g. molasses
- 3 g. dried yeast
- 4 g. salt
- 4 g. anise seeds The wheat and rye flours are sifted together and in a one quart metal bowl the molasses is dissolved in the coffee. The yeast, salt and anise seeds are added. The flour is added in steps to the liquid, and the mixture is worked into a dough ball. The dough ball is kneaded for about 5 minutes and then divided into 4 equal pieces, which are rolled out, balled and placed in a non-stick pan. The balls are flattened into round rolls which are allowed to rise in a warm location for about 45 minutes. The rolls are baked in an oven preheated to 325° F. for about 25 minutes, and then are stored in individual pint-size freezer bags and cooled in a freezer at −20° F. until needed for use.

To perform a gastric emptying test of the liquid phase, the patient fasts overnight. The next morning a baseline sample of breath is collected using the apparatus disclosed and claimed in the Opekun-Klein breath collection U.S. Pat. No. 5,140,993, issued Aug. 25, 1992 which is incorporated herein by express reference. The sample is transferred to an evacuated test tube in the kit, and then analyzed to obtain a baseline $^{13}CO_2$ level. To test the liquid phase for gastric emptying time, a 500 mg portion of $^{13}C$ labeled *Spirulina platensis* is added to 120 ml. bottle of white grape juice. The patient then spreads the cream cheese on the biscuit, made as disclosed herein, and consumes same. Immediately the patient also drinks the juice with the $^{13}C$ labeled matter suspended therein. The total caloric value of the test meal is about 340. Breath samples then are taken using the above-mentioned system, and are collected at about 10-minute intervals over the succeeding 2 hours or so. The samples are analyzed to obtain data points for a graph with the curve 10 as shown in the drawing FIGURE, which has change in concentration of $^{13}C$ in respiratory $CO_2$ as the ordinate and elapsed time as the abscissa. To test the solid phase for gastric emptying time, the method is performed as disclosed and claimed in my co-pending application for patent, referenced above. Breath samples again are taken to obtain data points similar to those shown for the lower curve 20 in the drawing FIGURE.

It now will be recognized that a new and improved non-invasive and radiation-free method and means has been disclosed for measuring gastric emptying of the liquid phase of food for diagnostic purposes. Certain changes and modifications may be made in the disclosed embodiment without departing from the inventive concepts involved. For example, a $^{14}C$ labeled molecule could be used, although $^{13}C$ is preferred. Thus, it is the aim of the appended claims to cover all such changes and modifications falling within the true spirit and scope of the present invention.

What is claimed is:

1. A method of measuring gastric emptying time of a liquid phase meal, comprising the steps of: preparing an edible alga of single cell organisms labeled with a carbon isotope by photosynthesis; suspending the alga in a liquid; having a patient consume said liquid and alga so that the carbon labeled nutrients therein are unable to penetrate the gastric mucosa and are absorbed in the small intestine and oxidized to labeled $CO_2$; and detecting the level of labeled $CO_2$ in breath samples taken from the patient at periodic intervals to determine the rate of gastric emptying of said liquid phase.

2. The method of claim 1 wherein said alga is *Spirulina platensis* which has been grown in an atmosphere of $^NCO_2$ where N is one of the numbers 13 or 14.

3. The method of claim 2 wherein said liquid is a fruit juice having a caloric value of a predetermined amount.

4. A drink to be consumed by a patient for a gastric emptying test, comprising: a selected quantity of a fruit juice having a predetermined caloric value, said juice having suspended therein, by mixing, a distinct quantity of single celled photosynthetic organisms that have been grown in an atmosphere that is substantially entirely $^NCO_2$, said single celled photosynthetic organisms being suspended in said juice so that the single celled photosynthetic organisms are unable to penetrate the gastric mucosa and thus pass into the small intestine with the juice so that when oxidized after digestion and absorption in the small intestine of a patient a detectible rise in the $^NCO_2$ content of the patient's breath is produced, N being one of the numbers 13 or 14.

5. The drink of claim 4 where the single celled photosynthetic organisms are *Spirulina platensis* alga.

6. A method of measuring gastric emptying time of the liquid phase of food consumed by a patient, comprising the steps of: preparing a biscuit having a calorie content of 150; preparing a drink to be consumed with said biscuit where a quantity $^NC$ alga comprising single celled photosynthetic organisms is mixed and suspended in a liquid so that the single celled photosynthetic organisms are unable to penetrate the gastric mucosa; having a patient consume said biscuit, a package of cream cheese and said drink as a meal having a caloric value of 340, so that said meal empties from the stomach into the small intestine where the labeled $^NC$ is digested, absorbed and oxidized to labeled $^NCO_2$; and then taking periodic breath samples from the patient to determine the rate of gastric emptying of the liquid phase of said meal.

7. The method of claim 6 wherein N is one of the numbers 13 or 14.

\* \* \* \* \*